United States Patent [19]

Hukins et al.

[11] Patent Number: 5,201,724
[45] Date of Patent: Apr. 13, 1993

[54] CATHETER

[75] Inventors: David W. Hukins, Chorltonville; Averil J. Cox, Bolton; Joanna M. Bibby, Hebdon Bridge; Terence M. Sutton, West Sussex; Ian Capstick, Essex, all of Great Britain

[73] Assignee: The Victoria University of Manchester, Manchester, England

[21] Appl. No.: 917,225

[22] Filed: Jul. 23, 1992

Related U.S. Application Data

[63] Continuation-in-part of Ser. No. 820,915, Dec. 23, 1991, abandoned, which is a continuation of Ser. No. 488,078, Jun. 22, 1990, abandoned.

[30] Foreign Application Priority Data

Dec. 23, 1987 [GB] United Kingdom ................ 8729977

[51] Int. Cl.$^5$ ............................................. A61M 5/32
[52] U.S. Cl. .................................. 604/265; 604/280
[58] Field of Search ............... 604/265, 266, 264, 280, 604/285; 424/422, 423, 426

[56] References Cited

U.S. PATENT DOCUMENTS

| | | | |
|---|---|---|---|
| 4,054,139 | 10/1977 | Crossley | 604/265 |
| 4,642,104 | 2/1987 | Sakamoto et al. | 604/265 X |
| 4,923,450 | 5/1990 | Maeda et al. | 604/265 |
| 4,960,415 | 10/1990 | Reinmuller | 604/265 |

FOREIGN PATENT DOCUMENTS 2120947 2/1982 United Kingdom.

Primary Examiner—John D. Yasko
Attorney, Agent, or Firm—Nies, Kurz, Bergert & Tamburro

[57] ABSTRACT

A medical catheter, for example, for drainage of a bodily fluid such as urine, includes a biodegradable portion which place in a body cavity, and thereby resists infection or the formation of encrustation or blockages normally associated with indwelling catheters.

22 Claims, 1 Drawing Sheet

CATHETER

This is a continuation-in-part of application Ser. No. 820,915 filed Dec. 23, 1991, now abandoned which is a continuation of application Ser. No. 488,078 filed Jun. 22, 1990 now abandoned.

This invention relates to catheters, in particular to medical catheters such as those employed in transferring fluids to or from a patient. Among the most common examples are those used in the lower or upper urinary tract or in the cardiovascular system.

In order to perform their required duty medical catheters must of necessity come into contact with the body organs and remain in place for a period of time which may be prolonged. Many problems however arise from the use of indwelling catheters. For example in the case of urinary drainage, a build-up can occur on the catheter of infecting bacteria or of crystalline deposits, this latter condition being known as encrustation or concretion. If the build-up leads to blockage of the catheter then the drainage of urine ceases and the catheter has to be prematurely removed, often with consideration discomfort to the patient and sometimes with associated damage to the lining of the organ through which the catheter passes and further resultant problems such as strictures and urethritis.

In the case of catheters used to introduce fluids into a patient, for example by intravenous feeding, it is important that the catheter is not also a source of introduction of infection.

Attempts have been made to prevent catheter-associated infection by known anti-bacterial treatments, but these tend not to be fully effective in removing infecting bacteria, for example those which secrete the enzymes known collectively as ureases. Such enzymes are a major factor in causing encrustation of urinary catheters. The introduction of an acidic solution to wash out the bladder can be effective in removing deposits but does not prevent a recurrence of the problem which created them.

Other proposals have included soaking or coating the catheter with such materials as silver salts, metallic silver and general antiseptic solutions. For example U.S. Pat. No. 4,054,139 describes and claims a catheter tube with a silver-bearing material on its exterior and interior surfaces.

Modifications have been proposed to catheters for other purposes, for example to assist insertion of a suprapubic catheter with minimum discomfort to the patient. Thus GB patent 2120947 describes and claims a catheter having a shaped fairing to facilitate entry of the catheter through tissue, the fairing being separable from the catheter upon withdrawal of the entry instrument and being of a urine-dispersible material such that it becomes flushed from the bladder during subsequent drainage.

In another example, U.S. Pat. No. 4,642,104 describes a urethral catheter having an antimicrobial substance chemically bonded as a layer to the inside wall of the catheter, so that the molecules are released as the chemicals bond breaks down. Such a layer is limited in thickness to about the dimensions of a single molecule since, once an antimicrobial substance is chemically bonded to a surface, it precludes the attachment of further molecules over that area.

The present invention is concerned with modifications to the material of the catheter so as to prolong the period over which the catheter can be left in place in the body before the onset of indwelling problems described above.

In its broadest aspect, the invention provides a catheter for drainage or collection of a bodily fluid which catheter comprises a portion which throughout its period of use is retained within a body cavity, in which at least part of the said portion includes a mass of solid biodegradable material in the form of a thick layer or plug.

The choice of biodegradable material and the manner in which it is incorporated into the catheter structure are dictated by the intended use of the catheter. The first requirement is for a material which will degrade or dissolve in the biological fluids to which it will be subjected. The choice can be made for example from such materials as polyglycolides, polylactides, polybutyrates, collagen, gelatin and hydrogels.

The essential element of a catheter is an elongated tube to provide a fluid-carrying lumen. For catheters according to the invention it is preferred to employ a composite structure including a tube of conventional (non-biodegradable) flexible material and to support the biodegradable material thereon or therein. Suitable materials for the supporting tube include natural rubber latex, polyvinyl chloride, polyurethane, polytetrafluoroethylene and silicone rubbers.

The usual form of catheter tube has two or more holes through the tube wall close to the distal end (i.e. within the body) to permit passage of a bodily fluid into the tube. At its proximal end (i.e. external to the body) it is usually provided with connection means for attachment to a drainage tube or reservoir. In general the connection means should not include any biodegradable material since biodegration at this point could lead to leakage or to detachment of the catheter tube from the associated tube or reservoir.

The biodegradable material must be either integral with any other material used in the catheter tube or be firmly affixed to the catheter tube.

The use of a biodegradable material according to the invention provides for an increase in the length of time for which a catheter can be retained without discomfort to the patient. By use in a variety of structures as described in greater detail below the biodegradation reduces the problems that otherwise occur with indwelling catheters, especially in terms of resisting infection, encrustation and blockage.

Within the preferred embodiment of a non biodegradable tube supporting a biodegradable material thereon or therein, the biodegradable material can for example be a layer on one or both of the outer and inner surfaces of the tube, a lining within the tube, a patch or patches on the tube surfaces, a stripe or stripes running along the tube surfaces, a plug or plugs in the tube, or any combination of these different configurations. For example, with the objective of preventing barriers to fluid flow, the biodegradable material can be applied as a multiplicity of layers within the tube such that as the deposits build up, the uppermost layer of the biodegradable material is shed in turn, taking the deposited material away with it and leaving a new outer layer of biodegradable material and a cleared passageway within the catheter.

The biodegradable material can be applied to the tube in combination with one or more additives which effect a medicating treatment within the body cavity in which the catheter is located. A variety of additives can be chosen with a view to achieving such benefits as inhibiting enzymes secreted by infecting bacteria, inhibiting the deposit of extraneous matter, dissolving deposited material, and achieving general anti-microbial, antiseptic or antibiotic action. For example acidic materials can be employed to acidify urine or accelerate the acidification process. Substances can be employed to inhibit or denature enzymes such as urease or to inhibit mineral deposition. Anti-microbial or antibiotic materials can be used to reduce infection and to target treatment in selected areas. Typical additives for use in such ways include citric acid, tartaric acid, citrates, acetohydroxamic acid, chlorhexidine and silver compounds.

In one embodiment of the invention, the biodegradable material is chosen from a substance which itself breaks down to produce the beneficial medical treatment. Thus for urine-removal catheters, biodegradable polymers can be utilised which hydrolyse in the urinary fluids to give acidic degradation products. Examples of such polymers are polylactides, polyglycolides and polybutyrates. The preferred polymers according to the invention for use in this application are poly-L-lactide, poly-L-glycolide and poly-3-hydroxybutyric acid. Such polymers give a continuous release of acidic materials into the urinary tract throughout the period in which the catheter is retained in place and thus provide an anti-crustation regime at all times.

In further preferred versions of the invention the medicating additive is a separate substance either absorbed in or encapsulated by the biodegradable material so as to give a controlled and continuous release of the additive as the biodegradation proceeds. Encapsulation can be achieved by several different forms of catheter having a composite construction. In one form the catheter tube is itself at least partially made of a material which is porous to the additive such that the additive is impregnated therein and the biodegradable material forms an encapsulating layer over the impregnated portion. Thus, in one preferred embodiment of the invention the biodegradable layer is laid over a porous support tube of non-biodegradable plastics material in a way that as it degrades under the action of the bodily fluids the porosity of the coated catheter tube increases, thereby permitting release of a medicating additive impregnated therein and to some extent compensating for barriers to fluid flow resulting from deposits on the tube surfaces. In another embodiment a layer of porous materials, for example of natural rubber latex foam, is first applied to the catheter tube, the additive is impregnated in the porous layer, for example by dipping the latex-coated tube into the material, and a layer of biodegradable material is applied over the porous layer. In a variation of this embodiment, the biodegradable material, for example in the form of solids granules, can itself be impregnated in the porous material rather than being present as an outer layer.

In such composite structures it is important to ensure that the biodegradable material is firmly secured either by mechanical means or adhesives, to the catheter tube, so that biodegradable material remains attached to the catheter tube throughout at least the greater part of the indwelling period. If desired a fibrous material such as cotton or cellulose may be incorporated into the matrix.

In a particularly convenient form of composite construction the biodegradable material is present as a plug located within the catheter tube at or immediately adjacent to the distal end and securely attached to the tube, for example by adhesive, by complementary shapes of the plug and tube or by a retaining membrane. Several different configurations of plug satisfy the requirements of the invention. Thus it can be for example (a) a single solid piece of biodegradable material,
(b) a shell of biodegradable material directly encapsulating a medicating additive, or
(c) a shell of biodegradable material enclosing a solid material impregnated with a medicating additive.

One advantageous configuration of tubular structure to ensure retention of the plug is an inner annulus within the tube adjacent to the plug.

The biodegradable material should be chosen according to the intended use of the catheter and in particular to the intended length of time for which the catheter is to be left in place in the body cavity. A range of rates of biodegradation, and thus control over the rate and period over which a beneficial material is released, is provided by choice of biodegradable material according to the rate at which it hydrolyses in the bodily fluids. For example in urine polybutyrates hydrolyse more slowly than polyglycolides which in turn hydrolyse more slowly than polylactides. It is also possible to reduce the biodegradability of such polymers by appropriate cross linking reactions during their production. Thus the invention conveniently provides for a catheter giving a controlled and continuous release of beneficial material over as prolonged period, for example 14 to 21 days or even longer.

The preferred quantity of beneficial material to be released from the catheter varies according to the material in question, to form the encapsulation and to the required rate of release. In general the quantity is within the range 10 to 1000 mg, the lower limit being dictated by the need to include sufficient material to be effective, the upper limit by the dimensions of the catheter. When present as a surface layer on the catheter tube the biodegradable material has a typical thickness in the range 20 to 40 $\mu$m and preferably extends over the whole of at least the inner surface of the portion of the catheter tube which is to be located in the body cavity.

The invention offers the advantage that the catheter can be safely left in place in its desired application for the indwelling period without fear of the onset of infection or build-up of blockages and thereby avoids the need for premature and painful removal in the event of troublesome complications.

It gives a controlled and continuous release of biodegradation products throughout the indwelling period, making it possible to prolong the indwelling period without discomfort to the patient, and in several preferred versions additionally gives a controlled and continuous release of medical treatment materials throughout the indwelling period.

The invention is described below with reference to the accompanying figures, in which.

Figure 1:
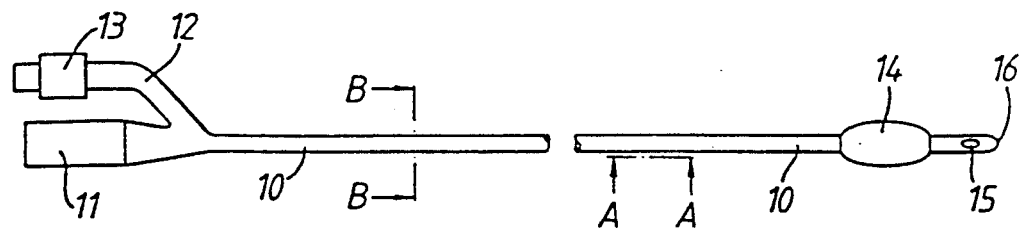
FIG. 1 is a general view of a tubular catheter of the type known as a Foley catheter and incorporating biodegradable material according to the invention so as to improve its properties for use as a urethral urine drain.
Figure 2:
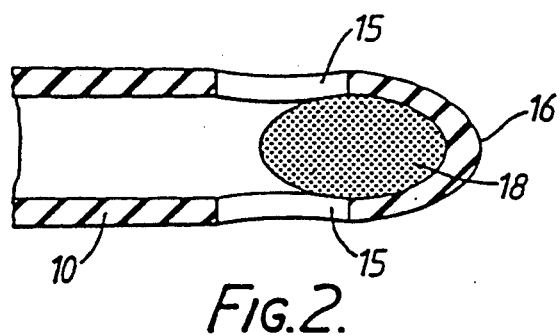
FIG. 2 is a sectional view of the tip of the catheter shown in FIG. 1.
Figure 3:
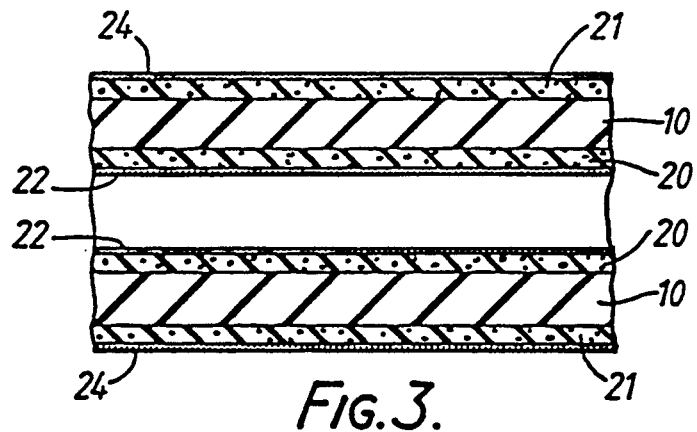

FIG. 3 shows in cross section a portion of the catheter of generally similar type to that shown in FIG. 1 and also for use in urethral urine drainage but with a different configuration of biodegradable material from that shown in FIG. 2. The portion illustrated in FIG. 3 is taken from a position equivalent to that indicated by lines A—A' in FIG. 1. In order to emphasise the cross sectional construction the dimensions in FIG. 3 are not strictly to scale.

Figure 4:
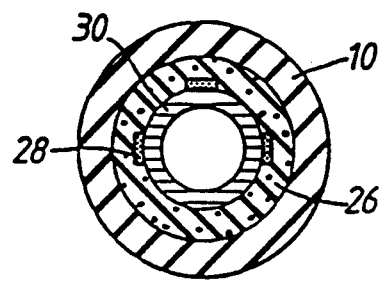

FIG. 4 is an enlarged cross sectional view, taken along a line equivalent to B—B' of FIG. 1 (but not showing the retention balloon 14), of a further type of internal construction for a catheter similar to that shown in FIG. 1.

The catheter shown in FIGS. 1 and 2 comprises a tube 10 of natural rubber latex having a connection funnel 11 for attachment to a drainage tube (not shown) and an inflation funnel 12, with associated valve 13, for use in the inflation of a retention balloon 14. The tube 10 has two oval-shaped eye holes 15 adjacent to its distal end 16 so as to permit urine drainage into the tube 10. The distal end 16 has a gently curved surface to facilitate insertion into the body cavity. A biodegradable plug 18 (not visible in FIG. 1) of ovoid shape and formed of poly-L-glycolide is located within the tube 10 at its distal end 16 and is secured firmly in place by a combination of the complementary shapes of its outer surface and the tube's inner surface and of an acrylic adhesive on the said surfaces. The plug 18 protrudes slightly into the urine channel provided by the eyeholes 15 and tube 10. The protrusion ensures good contact between the plug 18 and the urine flowing through the said channel. The catheter tube 10 is a 16 Charriére unit with an internal diameter of 2.7 mm and the eyeholes have an axial length of 6.7 mm. The biodegradable plug 18 has a volume of 15 mm$^3$.

Once the catheter has been inserted into the urethra and urine enters the drainage lumen, the urine begins the hydrolysis of the polyglycolide, thereby releasing glycolic acid into the urethra. The release continues through the period of retention of the catheter, which in this particular example is typically about 14 days.

The catheter having a portion as shown in FIG. 3 is generally similar to that shown in FIG. 1, i.e. it has a tube 10 of natural rubber latex, a connection funnel 11, an inflation funnel 12 and valve 13, and two oval-shaped eye-holes 15 adjacent its distal end 16. Unlike the version illustrated in FIG. 2 it does not include a biodegradable plug. Instead the tube 10 in this instance has inner and outer layers 20 and 21 respectively, of latex foam and biodegradable encapsulating layers, respectively 22 and 24, of poly-3-hydroxybutyric acid on the latex foam layers 20 and 21. Before application of the encapsulating layers 22 and 24, the tube 10 is dipped into chlorhexidine which is thereby impregnated with the foam layers 20 and 21. On a size 16 Charriére catheter as illustrated the layers 20 and 21 each have a thickness of 100 μm and the biodegradable layers 22 and 24 have an initial thickness of 25 μm.

When placed in the urethra a catheter of the type shown in FIG. 3 first undergoes hydrolysis of the biodegradable layers 22 and 24, which releases hydroxybutyric acid into the urine. As the hydrolysis proceeds however the layers 22 and 24 gradually reduce in thickness and allow the previously encapsulated chlorhexidine impregnated in the foam layers 20 and 21 to permeate through them and to effect an anti-microbial action in addition to the acidic treatment effected by the hydroxybutyric acid.

In the version of catheter illustrated in FIG. 4, the tube 10 is again externally similar to those described in FIGS. 1 to 3 but internally has a latex foam layer 26, three longitudinal stripes 28 of poly-L-glycolide and a lining 30 of hydrogel. The latex foam layer 26 is impregnated with an antibiotic material.

As the hydrogel biodegrades this version of catheter releases both antibiotic material from the foam layer 26 and acidic degradation products of the poly-L-glycolide stripes, thereby giving simultaneous treatment to inhibit infection and increase acidity.

Throughout the foregoing specification and in the appended claims, the term "encapsulated" is to be construed as including the containment within or behind a body of biodegradable material having a thickness in the order of microns, any substance which may be medically beneficial in use and which is capable of being released from within the material in the controlled and continuous manner as biodegration of the material occurs.

We claim:

1. A catheter for drainage or collection of a bodily fluid, which catheter comprises a tube of non-biodegradable flexible material having a portion which throughout its period of use is retained within a body cavity, characterized in that at least part of the said portion supports within the tube a solid biodegradable material which encapsulates or provides a medically beneficial substance which is thus released as a result of biodegradation, such that a controlled and continuous release of biodegradation products takes place throughout the said period when retained within the body cavity.

2. A catheter as claimed in claim 1, characterised in that biodegradable material is in the form of a multiplicity of layers within the tube.

3. A catheter as claimed in claim 1 or claim 2, characterized in that the tube also supports one or more additives which effect a medicating treatment within the body cavity.

4. A catheter as claimed in claim 3, characterised in that the or each additive is selected from citric acid, tartaric acid, acetohydroxamic acid, chlorhexidine and silver compounds.

5. A catheter as claimed in claim 3, characterised in that the or each additive is absorbed in the biodegradable material.

6. A catheter as claimed in claim 3, characterised in that the biodegradable material encapsulates the or each additive.

7. A catheter as claimed in claim 3, characterised in that the or each additive is impregnated in the material of the catheter.

8. A catheter as claimed in claim 7, characterised in that the tube supports a layer of porous material and the or each additive is impregnated in the porous layer.

9. A catheter as claimed in claim 1, characterised in that the tube supports a layer of porous material and the biodegradable material is impregnated in the porous layer.

10. A catheter as claimed in claim 1, characterised in that the biodegradable material is a lining within the tube.

11. A catheter as claimed in claim 1, characterised in that the biodegradable material is a patch or patches on the inner surface of the tube.

12. A catheter as claimed in claim 1, characterised in that the biodegradable material is a stripe or stripes running along the inner surface of the tube.

13. A catheter as claimed in claim 1, characterised in that the biodegradable material is in the form of a plug or plugs in the tube.

14. A catheter as claimed in claim 13, characterised in that the biodegradable material is in the form of a plug located within the catheter tube at or immediately adjacent to the distal end thereof and securely attached thereto.

15. A catheter as claimed in claim 14, characterised in that the plug is a solid piece of biodegradable material.

16. A catheter as claimed in claim 14, characterised in that the plug is a shell of biodegradable material directly encapsulating a medicating additive.

17. A catheter as claimed in claim 14, characterised in that the plug is a shell of biodegradable material enclosing a solid material impregnated with a medicating additive.

18. A catheter as claimed in claim 14, characterised in that the tube has an inner annulus adjacent to the plug.

19. A catheter as claimed in claim 1, characterised in that the biodegradable material is secured by adhesive means.

20. A catheter as claimed in claim 19, characterised in that a bonding aid is employed in association with the adhesive.

21. A catheter as claimed in claim 1, characterised in that the biodegradable material is of a type which degrades within the body cavity to effect a medicating treatment.

22. A catheter as claimed in claim 21, characterised in that the biodegradable material is selected from polylactides, polyglycolides and polybutyrates.

* * * * *

UNITED STATES PATENT AND TRADEMARK OFFICE
CERTIFICATE OF CORRECTION

PATENT NO. : 5,201,724

DATED : April 13, 1993

INVENTOR(S) : Hukins et al.

It is certified that error appears in the above-identified patent and that said Letters Patent is hereby corrected as shown below:

In the Abstract, line 3, after "which", insert --degrades throughout the period in which the catheter is in--.

Signed and Sealed this

Fourth Day of January, 1994

*Attest:*

BRUCE LEHMAN

*Attesting Officer*     *Commissioner of Patents and Trademarks*